United States Patent [19]
Pigiet et al.

[11] Patent Number: 4,771,036
[45] Date of Patent: Sep. 13, 1988

[54] METHOD AND OPHTHALMIC COMPOSITION FOR THE PREVENTION AND REVERSAL OF CATARACTS

[75] Inventors: Vincent P. Pigiet, Winchester, Mass.; Abraham Spector, New York, N.Y.

[73] Assignee: Trustees of Columbia University in the city of New York, New York, N.Y.

[21] Appl. No.: 828,112

[22] Filed: Feb. 10, 1986

[51] Int. Cl.$^4$ ............................................. A61K 37/02
[52] U.S. Cl. .................................... 514/17; 514/18; 514/912; 514/954
[58] Field of Search ................. 514/17, 18, 912–914, 514/954

[56] References Cited

U.S. PATENT DOCUMENTS 4,665,089  5/1987  Siezen et al. ........................ 514/425

OTHER PUBLICATIONS

Spector, A. and Roy, D. (1978) "Disulfide-Linked High Molecular Weight Protein Associated with Human Cataract" Proc. Natl. Aca. Sci. U.S.A., 75:3244–3248.

Garner, M. H. and Spector, A. (1980) "Selective Oxidation of Cysteine and Methionine in Normal and Senile Cataractous Lenses" Proc. Natl. Acad. Sci. U.S.A., 77:1274–1277.

Spector, A. (1984) "The Search for a Solution to Senile Cataracts" Invest. Ophthal. & Vis. Sci., 25:130–146.

Spector, A., Garner, M. H., Garner, W. H., Roy, D., Farnsworth, P. and Shyne, S. (1979) Science, 204:1323–1326, "An Extrinsic Membrane Polypeptide Associated with High-Molecular-Weight Protein Aggregates in Human Cataract."

Spector, A. and Garner, M. H. (1980) "Interaction of Human Cataract Fiber Cell Membrane Polypeptides with Cytoplasmic Components" In Developments in Biochemistry; Red Blood Cells and Lens Metabolism, S. K. Srivastava, Ed., 9:233–236, Elsevier North-Holland, N.Y.

Garner, M. H. and Spector A. (1980) "Sulfur Oxidation in Selected Human Cortical Cataracts and Nuclear Cataracts" Exp. Eye Res., 31:361–369.

Garner, W. H., Garner, M. H. and Spector, A. (1981) "Gamma-Crystallin, a Major Cytoplasmic Polypeptide Disulfide Linked to Membrane Proteins in Human Cataract" Biochem. Biophys. Res. Comm., 98:439–447.

Garner, W. H., Garner, M. H. and Spector, A. (1983) "$H_2O_2$-Induced Uncoupling of Bovine Lens $Na^+$, $K^+$-ATPase" Proc. Natl. Acad. Sci. U.S.A., 80:2044–2048.

Wannemacher, C. F. and Spector, A. (1968) "Protein Synthesis in the Core of Calf Lens" Exp. Eye Res., 7:623–625.

Dilley, K. J. and van Heyningen, R. (1976) "Some Aspects of Human Lens Metabolism: Glycolysis and Protein Synthesis" Doc. Ophthalmol. Proc. Ser., 8:171–175.

Hockwin, O. and Ohrloff, C. (1981) "Enzymes in Normal, Aging and Cataractous Lenses" in Molecular and Cellular Biology of the Eye Lens, H. Bloemendal, Ed. pp. 367–381, John Wiley & Sons, N.Y.

Spector, A., Scotto, R., Weissbach, H. and Brot, N. (1982) "Lens Methionine Sulfoxide Reductase" Biochem. & Biophys. Res. Comm., 108:429–434.

Brot, N., Weissbach, L., Werth, J. and Weissbach, H. (1981) "Enzymatic Reduction of Protein–Bound Methionine Sulfoxide" Proc. Natl. Acad. Sci. U.S.A., 78:2155–2158.

Brot, N., Werth, J., Koster, D. and Weissbach, H. (1982) "Reduction of N—Acetyl Methionine Sulfoxide: A Simple Assay for Peptide Methionine Sulfoxide Reductase" Anal. Biochem., 122:291–294.

Primary Examiner—J. R. Brown
Assistant Examiner—F. T. Moezie
Attorney, Agent, or Firm—Roman Saliwanchik; David R. Saliwanchik; John P. White

[57] ABSTRACT

The subject invention concerns a process for the prevention and reversal of cataracts. Specifically, the invention comprises the treatment of the eye lens with an effective cataract inhibiting amount of thioredoxin or thioredoxin-derived, or thioredoxin-like, dithiol peptide, alone, or in combination with a thioredoxin reductase regenerating system. The thioredoxin compound can be administered topically to a patient in need of such treatment on a daily basis over an extended period of time via known delivery techniques such as eye drops and ocular inserts.

8 Claims, No Drawings

METHOD AND OPHTHALMIC COMPOSITION FOR THE PREVENTION AND REVERSAL OF CATARACTS

The invention described herein was made with government support under Grant Number EYO4919 and EYO0423 from the National Eye Institute, National Institutes of Health, U.S. Department of Health and Human Services. The U.S. Government has certain rights in this invention.

BACKGROUND OF THE INVENTION

Cataract is an affliction of the lens of the eye. It is a very common problem in old age where it is referred to as senile cataract. Congenital cataract is generally found in young persons. A cataract is a partial or total opacity of the lens. Surgery, which involves removal of the lens, is generally a successful corrective means. The removal of the lens leaves primarily the cornea, to focus light upon the retina. This arrangement cannot provide sharp vision. However, use of contact lenses or glasses can provide a somewhat satisfactory substitute for the lens. The most common method of correcting this problem is to insert an intraocular artificial lens after removal of the cataract lens.

There remains a need for a therapeutic treatment of the lens which could prevent, or at least forestall, the development of cataracts. Advantageously, such a treatment could also be used for the reversal of cataracts. These desirable treatments are not now known in the art.

In order to possibly achieve such desirable treatments of the eye lens, the applicants have conducted extensive research on the nature of the lens itself. This research has led to some basic understanding of the eye lens as disclosed following.

Examination of normal and cataractous lenses indicates that while there is little oxidation in normal lenses, extensive oxidation occurs in a cataract, resulting in a high level of methionine oxidation to methionine sulfoxide and cysteine thiol oxidation to disulfide (Spector, A. and Roy, D. [1978] Proc. Natl. Acad. Sci. 75:3244–3248; Garner, M. H. and Spector, A. [1980] Proc. Natl. Acad. Sci. 77:1274–1277; Spector, A. [1984] Invest. Ophthal. & Vis. Sci. 25:130–146). Such oxidation occurs in the lens proteins, leading to the formation of disulfide linked high molecular weight aggregates which are capable of scattering light and producing a loss in lens transparency (Spector and Roy, 1978; Garner and Spector, 1980; Spector, A. Garner, M. H., Garner, W. H. Roy, D., Farnsworth, P. and Shyne, S. [1979] Science 204:1323–1326; Spector, A. and Garner, M. H. [1980] in developments in Biochemistry; Red Blood Cell and Lens Metabolism, S. K. Srivastava, ed., Vol. 9, pp. 233–236, Elsevier North-Holland, NY; Garner, M. H. and Spector, A. [1980] Exp. Eye Res. 31: 361–369). Some of these aggregates involve the linking, via disulfide bonds, of membrane components to components found within the cell (Spector and Garner, 1980; Garner and Spector, 1980; Garner, W. H., Garner, M. H. and Spector, A. [1981] Biochem. Biophys. Res. Comm. 98:439–447). The oxidation may also reduce or eliminate the activity of enzymes necessary for maintaining the viability of the tissue (Garner, W. H., Garner, M.H. and Spector, A. [1983] Proc. Natl. Acad. Sci. 80:2044–2048).

The lens is unique in having active metabolic activity and protein synthesis only in the outer region of the tissue. Thus, throughout much of the lens, oxidative insult to a protein molecule remains for the life of the tissue unless the insult can be repaired (Spector, A. [1984]Invest. Ophthal. & Vis. Sci. 25:130–146; Wannemacher, C. F. and Spector, A. [1968] Exp. Eye Res. 7:623–625; Dilley, K. J. and van Heyningen, R. [1976] Doc. Ophthalmol. Proc. Ser. 8:171; Hockwin, O and Ohrloff, C. [1981] In Molecular and Cellular Biology of the Eye Lens, H. Bloemendal, ed., p. 367, John Wiley & Sons, NY).

There are a number of systems that the lens employs to repair oxidative insult. For methionine sulfoxide, methionine sulfoxide peptide reductase is present which reduces the protein methionine sulfoxide back to methionine (Spector, A., Scotto, R., Weissbach, H. and Brot, N. [1982] Biochem. & Biophys. Res. Comm. 108:429–434; Brot, N., Weissbach, L., Werth, J. and Weissbach, H. [1981] Proc. Natl. Sci. 78:2155–2158; Brut, N. Werth, H. [1982] Anal. Biochem. 122:291–294). J., Koster, D. and Weissbach, This enzyme requires a dithiol as a co-factor reductant in order to function. It is believed that the physiological dithiol utilized is thioredoxin, a small protein of approximately 12,000 daltons (Spector, Scotto, Weissbach, Brot, 1982).

While a variety of systems are available to the cell to reduce disulfide bonds, protein disulfides are difficult to reduce and, generally, do not employ the same reducing systems as smaller components. Thus, for example, oxidized glutathione is reduced by glutathione reductase but this enzyme does not effectively reduce protein disulfides (Garner and Spector, 1980). Also, although it is known that thioredoxin and its co-factors thioredoxin reductase and nicotinamide adenine dinucleoside phosphate (NADPH) are capable of effectively reducing in vitro the disulfide bonds of a variety of proteins, including insulin and other protein disulfides, there has been no teaching or suggestion that such compounds can be used effectively in vivo.

BRIEF SUMMARY OF THE INVENTION

The subject invention concerns a novel process for the prevention and reversal of cataracts. Specifically, the invention process comprises the treatment of the eye lens with an effective cataract inhibiting amount of thioredoxin, or thioredoxin-derived, or thioredoxin-like, dithiol peptide, alone, or in combination with a thioredoxin reductase regenerating system (hereinafter these compounds being referred to as "thioredoxin compounds") to prevent the formation of cataracts, or, if a cataract is present, to reverse the course of the cataract formation. The treatment of the eye lens can be accomplished by any means known to treat eyes with medicaments. For example, the eye lens can be treated topically by application of the thioredoxin compounds via drops, ocular inserts, ointments, and the like.

DETAILED DISCLOSURE OF THE INVENTION

Upon administering an effective cataract inhibiting amount of thioredoxin, or thioredoxin-derived, or thioredoxin-like, dithiol peptide, alone, or in combination with a thioredoxin regenerating system (i.e., using a thioredoxin reductase) to an eye lens in need of such treatment, there is realized a prevention or retardation of cataract formation, or, if the lens is already cataractous, a reversal of the cataractous condition is realized.

Thioredoxins are low molecular weight dithiol proteins that have the ability to reduce disulfides in typical organic compounds such as Ellman's reagent or disulfides as they exist naturally in a variety of proteins (Holmgren, A. [1981] Trends in Biochemical Science, 6, 26-39).

Thioredoxin and thioredoxin-derived, or thioredoxin-like, dithiol peptides within the scope of the subject invention are exemplified by the following compounds:

(1) thioredoxin isolated from *Escherichia coli* (Laurent, T. C., Moore, E. C., and Reichard, P. [1964] J. Biol. Chem., 239, 3436-3445);

(2) thioredoxins isolated from other sources, e.g., thioredoxin isolated from yeast (Porque, G. P., Baldesten, A., and Reichard, P. [1970] J. Biol. Chem., 245, 2362-2379); *Cyanobacterium* (Gleason, F. K. and Holmgren, A. [1983] in "Thioreoxins, Structure and Function" [P. Gadal, ed.] Editions du Centre National de la Recherche Scientifique); rat (Guerara, J., Moore, E. C., and Ward, D. NM. [1983] ibid; T4 bacteriophage (Soderberg, B-O, Sjoberg, B-M, Sonnerstam, U., and Branden, C-I [1978] Proc. Natl. Acad. Sci. USA, 75, 5827-5830); purification of mammalian thioredoxin (Luthman, M. and Holmgren, A. [1982] Biochem. 121:6628-6633);

(3) thioredoxin-derived dithiol peptides representing peptides produced by cleavage of intact thioredoxins, as described in Example 1, infra. One such example of this class of thioredoxin-derived peptides is the fragment containing residues 1 through 37 (i.e., $T_{1-37}$) produced by cyanogen bromide cleavage of thioredoxin from *E. coli*. The important feature of these thioredoxin-derived, and thioredoxin-like, dithiol peptides is that they contain the redox-active peptide sequence, Cys-X-Y-Cys, wherein X and Y can be any of the 20 amino acids. For example, the redox-active peptide sequence from *E. coli* thioredoxin is Cys-Gly-Pro-Cys (Cys=cysteine, Gly=glycine, Pro=proline). Also the redox-active sequence, Cys-Gly-Pro-Cys-Lys can be used (Lys=lysine); and (4) thioredoxin-like dithiol peptides that have the intrinsic ability to catalyze the reduction of protein disulfides. These thioredoxin-like dithiol peptides will generally have the characteristic of containing a pair of cysteine residues which form a redox-active disulfide. This example includes peptides, derived from natural sources or constructed synthetically, that include the same redox-active peptide sequence disclosed above, for example, as in *E. coli* thioredoxin, Cys-Gly-Pro-Cys or Cys-Gly-Pro-Cys-Lys, or analogous sequences from other thioredoxins such as that encoded for by T4 bacteriophage, Cys-Val-Tyr-Cys (Cys-cysteine, Val=valine, Tyr=tyrosine) (Soderberg, B-O, Sjoberg, B-M, Sonnerstam, U., and Branden, C-I [1978] Proc. Natl. Acad. Sci. USA, 75, 5827-5830). Other thioredoxin-like peptides include the class of seed proteins called purothionins that have intrinsic thioredoxin-like activity (Wada, K. and Buchanan, B. B. [1983] in "Thioredoxins, Structure and Function" [Gadal, P., ed], Editions du Centre National de la Recherche Scientifique).

The concentration of thioredoxin or one of the thioredoxin-derived, or thioredoxin-like, dithiol peptides which can be used in the invention process ranges from about 0.01 to about 10 mM. The optimal concentration for oxidized intact bacterial thioredoxin appears to be at least 0.01 $\mu$M. Mammalian thioredoxin levels can be expected to be lower.

It should be recognized that the precise level of thioredoxin or thioredoxin-derived, or thioredoxin-like, dithiol peptide can be readily ascertained by a person skilled in the art having possession of the subject invention. Factors such as age and general health condition of the patient to whom the thioredoxin compound is being administered must be considered. Thus, a patient less than 10 years of age will be treated with a concentration of a thioredoxin compound which will be less than that used for an older patient. Likewise, treatment of a cataractous lens will necessitate a higher concentration of thioredoxin compounds than that which would be used for a pre-cataractous lens treatment. These variations in concentration can be adjusted readily by the skilled practitioner. In treating patients over the age of 10 years, the concentration of thioredoxin compounds will be about 0.01 to about 10 mM.

The thioredoxin compounds can be administered to the eye lens by known means of administering other medicaments to the eye. For example, the thioredoxin compounds, suitable formulated, can be administered in the form of eye drops or with ocular inserts. Suitable formulations will incorporate standard eye vehicles which are physiologically acceptable to the eye. Such vehicles can be solutions or ointments, as desired. Further, the thioredoxin compounds can be formulated in unit dosage form with non-active opthalmologically-acceptable carriers well known in the art, or with other active medicaments where treatment of other conditions of the eye, for example, infection, allergy or inflammation, is prescribed.

The term "unit dosage form" as used herein refers to physically discrete units suitable as unitary dosages for human and animal subjects, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans. Examples of suitable unit dosage forms in accord with this invention are tablets, capsules, ocular inserts, dropperfuls, segregated multiples of any of the foregoing, and other forms as are known in the art.

The thioredoxin compound can be easily prepared in unit dosage form with the employment of pharmaceutical materials which themselves are available in the art and can be prepared by established procedures.

The thioredoxin compounds can be administered daily depending on the conditions being treated. For example, treatment of a lens where no evidence of cataract is present can be made daily by eye drops using a minimal effective cataract-inhibiting amount of thioredoxin compound. Such a treatment can be carried on for a number of years since thioredoxin is not known to have toxic manifestations at low concentration levels. For treatment of lenses with cataracts, the concentration of thioredoxin compound can be increased and maintained until there is evidence of reversal of the condition. Thus, when treating a cataractous lens, it is necessary that such treatment be under the control of a trained ophthalmologist who can readily make the proper treatment adjustments as conditions warrant. Again, these procedures must take into account the overall condition of the patient and severity of the cataract affliction, as a physician would normally do in treating any affliction. The details set out herein when coupled with a physician's skills will readily enable the physician to maximize the treatment regime for a particular patient.

Thioredoxin is purified either from a commercial source of *E. coli*, strain B (Grain Processing Corp., Minneapolis, MN) or from any of a number of common strains of *E. coli* grown by standard procedures (Pigiet, V. and Conley, R. R. [1977] J. Biol. Chem., 252, 6367–6372). The protein is purified using standard procedures including chromatography on ion exchange and molecular seive columns (Williams, C. H., Zanetti, G., Arscott, L. D. and McAllister, J. K. [1967] J. Biol. Chem. 242, 5226–5231; McEvoy, M., Lantz, C., Lunn, C. A. and Pigiet, V. [1981] J. Biol. Chem. 256, 6646–6650).

Thioredoxin protein is assayed immunologically using quantitative rocket immunoelectrophoresis as described in McFvoy et al., supra.

Following are examples which illustrate the process of the invention, including the best mode. These examples should not be construed as limiting. All solvent mixture proportions are by volume unless otherwise noted.

EXAMPLE 1

Thioredoxin Fragments $T_{1-37}$ and $T_{19-36}$ (a) Production of $T_{-37}$ BY Cyanogen Bromide Cleavage A sample of *E. coli* thioredoxin was dialyzed in water for 12 hr at 4° C. Five ml was dried and resuspended in 70% formic acid. Cyanogen bromide (Sigma Chemical) was dissolved in 70% formic acid and added to thioredoxin in a 50-fold molar excess of methionine. The solution was purged with nitrogen and incubated at room temperature in the dark for 24 hr. At the completion of the cleavage reaction the solution was dried under nitrogen, resuspended in sodium acetate buffer and adjusted to pH 8.5 with ammonium hydroxide.

Samples were loaded onto a Waters μ-Bondapak C-18 column (Trademark of Waters Associates, Inc., Milford, MA) attached to a Beckman Model 421 system (Trademark of Beckman Instruments, Inc., Fullerton, CA) monitored at 214 nm. The solvent system employed was 0.1% trifluoroacetic acid (Buffer A) and 0.08% trifluoroacetic acid in acetonitrile (Buffer B). A gradient from 0% to 60% B over 30 min was used to separate the peptides at a flow rate of 2 ml/min.

Thioredoxin was cleaved by CNBr into two fragments, $T_{1-37}$ and $T_{38-108}$, eluting at 44% and 51% buffer B, respectively. Amino acid analysis identified and confirmed the composition of both peptides. (Holmgren, A and Reichard, P. [1967] Eur. J. Biochem. 2, 187–196) $T_{1-37}$ contained the active site of the enzyme. The two peptides recovered accounted for 69% of the starting material. Unreacted thioredoxin accounted for 12–15% of the loss, while HPLC separation may be responsible for the additional losses.

(b) Production of $T_{19-36}$ by Trypsin Cleavage

After HPLC separation, described above, $T_{17}$ was pooled, dried, and resuspended in sodium acetate buffer and adjusted to pH 8.0 with NH$_4$OH. An aliquot of trypsin (Sigma Chemical) was added to the incubation at 1% (w/w) of peptide concentration. The reaction mixture was incubated at 37° C. for 1 hr. Separation of trypsin fragments was done by HPLC as for the cyanogen bromide fragments.

Trypsin digestion of the $T_{1-37}$ peptide yielded two peptides, $T_{4-18}$ and $T_{19-36}$, which were resolved by HPLC, eluting at 31% and 45% in buffer B, respectively. Amino acid analysis revealed that the species eluting at 31% B contained 15 amino acids and corresponds to the active site peptide, $T_{19-36}$. Incubation of 90 nmoles of $T_{1-37}$ produced 80 nmoles $T_{1914\ 36}$ after separation by HPLC with a yield of 88%.

EXAMPLE 2

Utilizing 2', 5' ADP-Sepharose, lens homogenates were shown to contain thioredoxin reductase and, thus, have available the system necessary to recycle added thioredoxin. Use of 2', 5' ADP-Sepharose for the affinity purification of lens thioredoxin reductase followed the general principles outlined by Pigiet and Conley (Pigiet, V. and Conley, R. R. [1977] J. Biol. Chem. 252:6367–6372). 20 gm of the outer region of the lens, the cortex, was homogenized in 50 mM Tris pH 7.5, 10 mM β-mercaptoethanol; the insolubles were removed by centrifugation and the supernatant passed through a G-25 column to remove low molecular weight components, utilizing 25 mM KCl, 10 mM NaCl, 1.1 mM MgCl$_2$, 0.1 mM ethylenediaminetetraacetic acid (EDTA), 10 mM 4-(2-hydroxyethyl)-1-piperazine ethanesulfonic acid (HEPES) pH 7.2 (buffer A). It was then loaded on a 2', 5' ADP-Sepharose column (0.75 × 13 cm) equilibrated with buffer A. After elimination of the non-binding components, 0.1 M KCl, 2 mM NADPH in buffer A was used to elute the thioredoxin reductase. The material was then assayed with the addition of thioredoxin by the 5', 5'-dithiobis (2-nitrobenzoic acid) (DTNB) (Sigma Chemical, St. Louis, MO) methodology. Recoveries of thioredoxin reductase were approximately 40%.

The results suggest that there is approximately 0.6 units of activity per mg protein in the lens, suggesting a level of activity approximately 1/100 that of the liver. The important point is that the enzyme is present in the lens.

EXAMPLE 3

Because of the low level of thioredoxin presumed to be present in the tissue, an attempt was made to increase the thioredoxin level in the tissue.

This was done by utilizing *E. coli* thioredoxin which is active with the mammalian thioredoxin reductase. $6 \times 10^5$ to $2 \times 10^6$ lens epithelial cells were incubated 15 hr in the presence of 0.4 μmoles thioredoxin per ml of Eagle's medium (Gibco Division, Chagrin Falls, OH) with 10% fetal bovine serum. From 300 to 400 pmoles of thioredoxin can be detected by the rocket immunochemical assay technique. Values of the same magnitude can be observed by the DTNB-insulin assay. The latter results indicate that the thioredoxin retains its activity after being incorporated into the lens epithelial cells. Separation of the washed cells into membrane and cytosol fractions shows that approximately 40% of the activity is associated with the membrane fraction. No activity was detected in the final wash.

Cell cultures were prepared as described by Spector et al. (Spector, A., Huang, R-R. C. and Wang, G-M [1985] Curr. Eye Res. 4:1289–1295).

EXAMPLE 4

Experiments were also performed to assess the ability of the thioredoxin system to reduce disulfides in a lens protein. Gamma crystallin, a lens protein frequently observed in the disulfide-linked high molecular weight aggregates, was examined.

Gamma crystallin was prepared by the following procedure: Bovine lenses weighing approximately 1.4 gm were used within 3 hr of slaughter. The eyes were kept at 4° until use. The lenses were dissected out of the eyes, the capsule-epithelium carefully removed and the outer 50% of the lens was then utilized. Approximately 8 gm of the cortex was homogenized in 32 ml of 50 mM Tris, pH 7.4, 10 mM $\beta$-mercaptoethanol. The homogenate was centrifuged at 105,000 g for 60 min. 30 ml of the supernatant containing 1.5 gm of protein was loaded on a CL6B column (Pharmacia, Piscataway, NJ), equilibrated with 50 mM Tris, pH 7.4, 10 mM $\beta$-mercaptoethanol, 0.1 M NaCl and run with the same buffer. The gamma crystallin elutes as a discrete peak after the alpha and beta crystallin fractions. The elution was followed by 280 mu absorption of the fractions. Confirmation of the assignment of peaks was made by gel electrophoresis profiles. The protein solution was dialyzed and then lyophilized.

Utilizing gamma crystallin preparations which contained a disulfide bond, it could be shown that the disulfide was effectively reduced by the thioredoxin system. The assay used was analogous to the insulin reduction assay, except that activity of disulfide reduction was measured by the consumption of NADPH (monitored as the decrease in absorbance at 340 nm). In comparison to the reduction of insulin, a polypeptide rapidly reduced by thioredoxin, under comparable conditions, the gamma crystallin is reduced at an initial rate approximately $\frac{1}{8}$ that of insulin. Furthermore, if the reducing capability of dithiothreitol (DTT), a commonly used disulfide reducing agent, was compared to the thioredoxin system, it was found that concentrations of thioredoxin of 6 $\mu$M were 2.5 times more effective in reducing gamma crystallin than 1 mM DTT, a DTT concentration 166-fold higher than that of thioredoxin concentration. Glutathione, the commonly-found physiological thiol present in lenses in high concentration, is even much more inefficient in reducing protein disulfides than is DTT.

The data support the contention that the addition of thioredoxin to the lens will effectively increase the ability of the tissue to withstand oxidative insult.

We claim:

1. A process for the prevention and reversal of cataracts which comprises treating cells of mammalian eye lens with an effective cataract inhibiting amount of thioredoxin or thioredoxin-derived, or thioredoxin-like compound all from *Escherichia coli*, alone, or in combination with a reductase which reduces said thioredoxin, thioredoxin-derived or thioredoxin-like compound in association with an ophthalmologically acceptable carrier.

2. A process, according to claim 1, wherein said treatment is a topical treatment.

3. A process, according to claim 1, wherein said effective cataract inhibiting amount of thioredoxin or a thioredoxin-derived or thioredoxin-like, dithiol peptide is about 0.01 mM to about 10 mM.

4. A process, according to claim 1, wherein said thioredoxin-derived dithiol peptide is the fragment containing residues 1 through 37 produced by cyanogen bromide cleavage of *Escherichia coli* thioredoxin.

5. A process, according to claim 1, wherein said thioredoxin-derived dithiol peptide is the fragment containing residues 19 through 36 produced by trypsin digestion of residues 1 through 37 produced by cyanogen bromide cleavage of *Escherichia coli* thioredoxin.

6. A process, according to claim 1, wherein said thioredoxin-derived, or thioredoxin-like, dithiol peptide comprises the redox-active peptide sequence Cys-X-Y-Cys-Lys or Cys-X-Y-Cys, wherein X and Y can be any of the 20 amino acids.

7. A process, according to claim 6, wherein said redox-active peptide sequence is Cys-Gly-Pro-Cys-Lys.

8. A composition of matter for the prevention and reversal of cataracts comprising thioredoxin or thioredoxin-derived, or thioredoxin-like, dithiol peptide from *Escherichia coli*, alone, or in combination with a reductase which reduces said thioredoxin, thioredoxin-derived or thioredoxin-like dithiol peptide in association with an ophthalmologically acceptable carrier wherein the concentration of the thioredoxin, thioredoxin-derived or thioredoxin-like compound is about 0.01 to about 10 mM.

* * * * *